(12) United States Patent
Fell

(10) Patent No.: US 6,733,433 B1
(45) Date of Patent: May 11, 2004

(54) BLOOD SEPARATION SYSTEM PARTICULARLY FOR CONCENTRATING HEMATOPOIETIC STEM CELLS

(75) Inventor: Claude Fell, Nyon (CH)

(73) Assignee: Biosafe S.A., Eysins (CH)

( * ) Notice: Subject to any disclaimer, the term of this patent is extended or adjusted under 35 U.S.C. 154(b) by 0 days.

(21) Appl. No.: 09/869,131
(22) PCT Filed: Dec. 24, 1999
(86) PCT No.: PCT/IB99/02053
§ 371 (c)(1), (2), (4) Date: Jul. 30, 2001
(87) PCT Pub. No.: WO00/38762
PCT Pub. Date: Jul. 6, 2000

(30) Foreign Application Priority Data

Dec. 24, 1998 (WO) .................... PCT/IB98/02114

(51) Int. Cl.[7] .................. B04B 1/02; B04B 5/04; B04B 11/00; B04B 13/00
(52) U.S. Cl. .................. 494/37; 494/1; 494/2; 494/10; 494/37; 494/43; 494/56; 435/2
(58) Field of Search .................. 494/1, 2, 10, 37, 494/43, 45, 47, 48, 50, 56, 63, 67; 435/2; 604/408, 410, 604, 6.1, 9

(56) References Cited

U.S. PATENT DOCUMENTS 3,737,096 A 6/1973 Jones et al.
4,946,434 A 8/1990 Plaisted et al. ............ 494/29
5,368,542 A 11/1994 McMannis et al. ......... 494/45
5,641,622 A 6/1997 Lake et al. ................. 435/2
6,123,655 A * 9/2000 Fell ........................... 494/50

FOREIGN PATENT DOCUMENTS

WO 97 15399 5/1997

* cited by examiner

Primary Examiner—John Kim
(74) Attorney, Agent, or Firm—Sturm & Fix LLP

(57) ABSTRACT

A system for separating biological fluids into components, comprises a set of containers for the biological fluid to be separated and the separated components, optionally an additional container for additive solution, and a hollow centrifugal processing chamber having an axial inlet/outlet for the biological fluid. The processing chamber contains a piston movable to intake a selected quantity of biological fluid and express processed biological fluid components via the outlet. Optical means monitor the position of piston to control the amount of intaken fluid and the expression of components. A distribution valve arrangement selectively communicates the processing chamber and the containers or places them out of communication. The system is arranged to operate in a seperation mode and in a non-separation transfer mode, especially for adding preservative solution to separated blood stem cells.

22 Claims, 7 Drawing Sheets

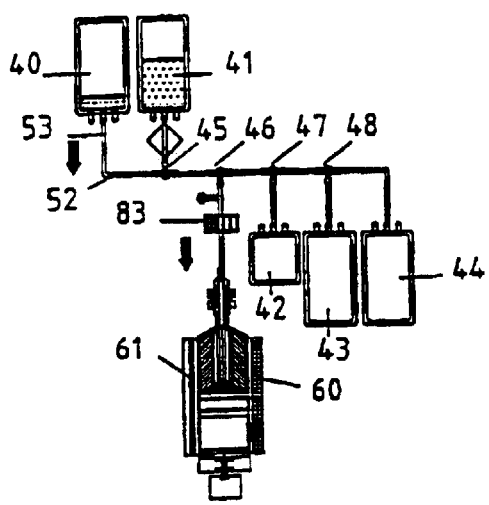
Fig. 9.1
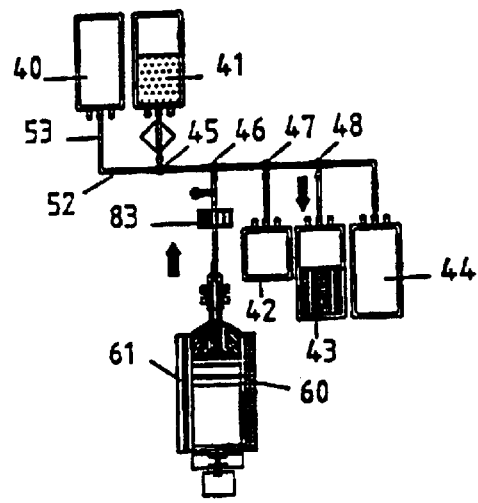
Fig. 9.2
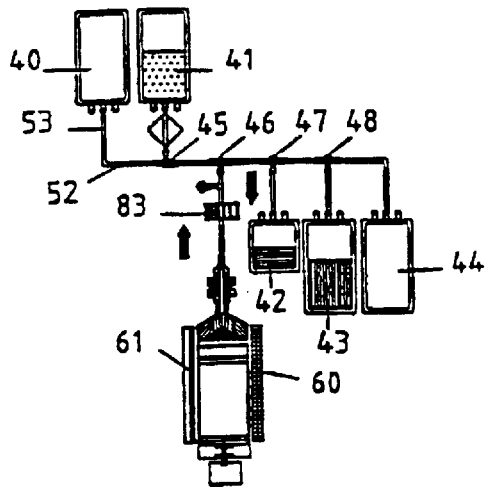
Fig. 9.3
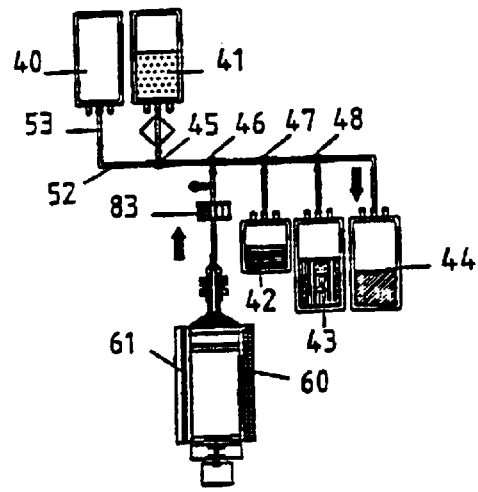
Fig. 9.4
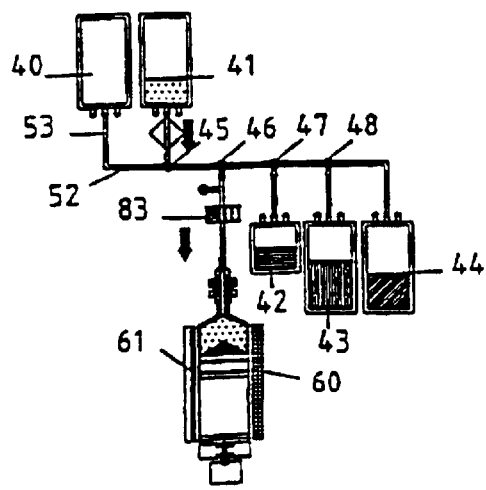
Fig. 9.5
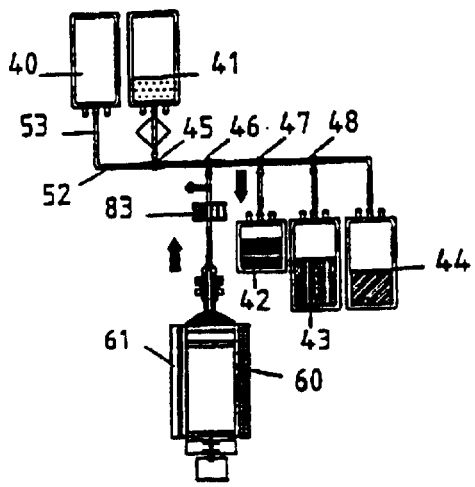
Fig. 9.6

BLOOD SEPARATION SYSTEM PARTICULARLY FOR CONCENTRATING HEMATOPOIETIC STEM CELLS

CROSS-REFERENCE TO RELATED APPLICATIONS

This application is the national phase application of International Application No. PCT/IB99/02053 filed Dec. 24, 1999, entitled "Blood Separation System Particularly for Concentrating Hematopoietic Stem Cells." Priority is claimed to the PCT application filing date under 35 U.S.C. § 365.

FIELD OF THE INVENTION

This invention relates to the automated processing and separation of biological cells as found in whole blood, and relates more specifically to a functionally closed system allowing to extract certain cell populations like hematopoietic stem cells, for immediate use or their mixing with an additive solution or a storage solution for later separate storage operations and to the methods for carrying out such an extraction.

BACKGROUND OF THE INVENTION

Blood separation systems and methods have emerged over the past 20 years in response to the growing need for efficient blood component therapies. Among them are the transplantation of hematopoietic progenitor stem cells, which in many cases is the only remaining cure to oncological disorders. Patients in need of a stem cell transplant have mainly three options:

1) Adult bone marrow stem cells;
2) Peripheral blood stem cells found in the circulatory system;
3) Stem cells found in umbilical cord and placental blood retrieved at birth of a new born infant.

For most stem cell transplants, the main limitation has been the risk of graft-versus-host-disease (GVHD), requiring an excellent HLA-match tissue (HLA=Human Leucyte Associated).

Umbilical cord blood is a rich source of the primitive hematopoietic stem and progenitor cells, with extensive proliferation capacity and capacity to self-renew. This field has advanced rapidly from clinical implants utilizing only HLA-matched grafts to unrelated donor cell transplants which open a much larger indication for stem cell transplantation. This increase in clinical experience with cord blood is due mainly to the establishment of banks for storage of hematopoietic stem cells from unrelated umbilical blood cord.

Blood volumes recovered from umbilical cord are usually very low (40 to 150 ml) and there is some concern that any attempt at product manipulation and concentration might result in stem cell loss, which might impair engraftments. Therefore umbilical cord blood is sometimes stored as is, with preservative solution added. A much preferred way would be to eliminate most unwanted cells like red cells and white cells, resulting in a considerable volume reduction. Less preservative solution would be required, smaller bags, smaller storage spaces would be used and considerable energy savings achieved, all of this translating in substantial cost savings. The quality of the stem cell product when retransfused would be improved as well, as lysed cells resulting from storage would be drastically reduced.

No device or automated system exists for processing and concentrating on line umbilical cord stem cells. There is nevertheless a considerable interest for concentrating umbilical cord blood stem cells without loss or altering their functionality.

EP-B-0 912 250 (C. FELL), the contents whereof are herein incorporated by way of reference, describes a system for the processing and separation of biological fluids into components, comprising a set of containers for receiving the biological fluid to be separated and the separated components, and optionally one or more additional containers for additive solutions. A hollow centrifuge processing chamber is rotatable about an axis of rotation by engagement of the processing chamber with a rotary drive unit. The processing chamber has an axial inlet/outlet for biological fluid to be processed and for processed components of the biological fluid. This inlet/outlet leads into a separation space of variable volume wherein the entire centrifugal processing of biological fluid takes place. The processing chamber comprises a generally cylindrical wall extending from an end wall of the processing chamber, this generally cylindrical wall defining therein the hollow processing chamber which occupies a hollow open cylindrical space coaxial with the axis of rotation, the axial inlet/outlet being provided in said end wall coaxial with the generally cylindrical wall to open into the hollow processing chamber. The processing chamber contains within the generally cylindrical wall an axially movable member such as a piston. The separation space of variable volume is defined in an upper part of the processing chamber by the generally cylindrical wall and by the axially movable member contained in the generally cylindrical wall of the processing chamber, wherein axial movement of the movable member varies the volume of the separation space, the movable member being axially movable within the processing chamber to intake a selected quantity of biological fluid to be processed into the separation space via the inlet before or during centrifugal processing and to express processed biological fluid components from the separation space via the outlet during or after centrifugal processing. Means are provided for monitoring the position of the movable member to thereby control the amount of intaken biological fluid and the expression of separated components. The system further comprises a distribution valve arrangement for establishing selective communication between the processing chamber and selected containers or for placing the processing chamber and containers out of communication.

The system according to EP-B-0 912 250 is designed to operate for the separation of biological fluids, and has proven to be very polyvalent for many separation applications, especially for on-line separation of components from a donor or a patient.

DISCLOSURE OF THE INVENTION

According to the invention, such system is arranged to operate in a separation mode and in a non-separation transfer mode, which provides greater possibilities for use of the system including new applications which were heretofore not contemplated, such as separation of hematopoietic stem cells and in general laboratory processing. According to the invention, the system is arranged to operate such that:

in the separation mode fluids can be intaken into the processing chamber while the chamber is rotating or stationary, fluid intaken into the chamber is centrifuged and separated into components, and the separated components expressed while the chamber is rotating or, optionally, for the last separated component, while the chamber is stationary; and in the transfer mode the processing chamber intakes fluid and expresses fluid with the chamber stationary, The valve actuation arrangement is actuable to transfer amounts of fluid from one container to another via the processing chamber, by moving he member, without centrifugation or separation of the fluid into components, and the means for monitoring the position of the movable member controls the amounts of non-separated fluids transferred.

Further features of the invention are set out in the claims. This invention thus proposes a functionally closed processing kit associated with a portable apparatus, whose function is to monitor and automate the procedure. The kit, usually disposable for avoiding the likelihood of disease transmission, is based on a centrifugal processing chamber whose volume can be varied during operation, allowing to adjust to the exact quantity of blood to process. Such variable volume chamber is described in the aforementioned EP-B-0 912 250 (C. FELL). The chamber is connected to a set of bags and tubing lines for the collection of the separated components. The blood bag containing the blood to process is generally connected to the disposable set through the use of a sterile connecting device, or an aseptic connection under laminar flow. It is however possible to have this bag prefilled with anticoagulant and preconnected to the disposable kit.

A bag containing an additive solution can be connected to the disposable kit via a bacterial filter. The other bags are provided for the collection of the separated components. The stem cell collection bag material is optimally chosen for the storage conditions.

The tubing line selection for conveying the separated products into the proper bags is accomplished by a set of rotational valves called stopcocks that can be arranged in a manifold array, or by a single multiport rotational valve, forming part of the set. Such an arrangement allows to eliminate any cross-contamination between adjacent lines when using standard pinch valves.

The above-mentioned disposable kit cooperates with an instrumentation for monitoring and automating the process, for instance as described in EP-B-0 912 250 (C. FELL). The centrifuge drives a rotating disk which receives the centrifugal processing chamber and locks it in place. Its closing cover will grip and hold she housing of the rotary seal of the processing chamber.

An optical sensor made of an array of LED and corresponding receiving sensors placed at 180° is implemented vertically on the side of centrifuge, for monitoring the piston position. Volumes intaken into or extracted from the chamber can therefore be exactly measured. The topdeck receives an optical line sensor module which monitors the color in the effluent tubing, feeding-back this information to the control program. An array of shafts equipped with fittings for driving a set of multiple stopcock valves protrude from the top deck. They are coupled to a set of motors enabling the tubing line selection. Encoders are attached to the motors for monitoring the stopcock valves position. The front panel incorporates a window allowing the user to see displacement of the piston in the chamber.

The procedure for extracting stem cells out of an umbilical cord is as follows. Initially blood is recovered from the umbilical cord at birth and collected aseptically into a plastic bag, with anticoagulant added like Citrate-Phosphate-Dextrose CPD-1 to avoid clotting. After initial sampling is taken to assess its richness in stem cells, the bag is sterile or aseptically connected to the processing kit and the whole set is loaded onto the separation system, which initially operates in the separation mode or the transfer mode at choice. In the separation mode the centrifuge starts driving the separation chamber at around 4000 rpm, and blood is introduced by moving down the chamber piston pneumatically. Two cases can then occur. If the volume of blood to process is smaller than the processing chamber volume (as detected by the empty state of the effluent tubing), the piston is maintained at an intermediate position pneumatically, monitored by the piston position sensor. If the volume of blood completely fills the separation chamber, detected by the piston reaching the bottom of the chamber, the pneumatic compressor stops. In both cases, centrifugation speed is increased to around 6000 rpm to shorten the sedimentation time to 5–8 min. After this period, centrifugation slowly decreases to around 4000 rpm. Stopcocks are rotated to allow the collection of the separated products, and the pneumatic pressure gradually increases to move the piston upwards. The speed of the piston remains low, actively monitored by she piston position sensor, in order to maintain the sedimentation profile of the cells within the chamber. The first milliliters from the inlet line are purged in the stem cell bags. Plasma is extracted then collected into a first bag. It is followed by platelets, packed in the intermediate layers, or buffy-coat. Apparition of the first platelets is detected by the optical line sensor monitoring the effluent line tubing. At that moment, the product, very rich in stem cells, is directed into a second collection bag by rotating a stopcock valve. A volume counter is started, which depends among other factors on the total blood volume processed. When this counting volume has been reached, centrifugation is stopped. The proper stopcock valve is rotated and the last product is extracted, essentially a volume of packed red cells with residual granulocytes, into a third collection bag. Another cycle can then resume if the umbilical cord blood has not been totally processed. Otherwise, the separation and stem cells collection process is completed at this stage.

However, it is possible to reprocess the content of the bag containing the stem cells, in view of further purifying the product. In this case, the proper stopcock valve is rotated to intake the content of the stem cell concentrate bag. The procedure to collect stem cell rich layer is identical then to the one described above.

Another alternative to isolate the stem cell rich fraction from the buffy-coat is by using density gradient products such as those available under the names Ficoll and Percoll. In this alternative, a density gradient product is first introduced into the processing chamber, followed by introduction of whole blood, and a component of the biological fluid is separated into a giver container and its collection is completed when the density gradient appears. Possibly the density gradient product may be introduced during processing.

Using Ficoll would for example consist of first introducing the density gradient into the processing chamber, followed then by whole blood. After complete introduction of blood into the chamber, a sedimentation period of a few minutes is started. Stem cells and platelets form an interface in front of the gradient, whereas erythrocytes and granulocytes have passed through the Ficoll and are held against the walls of the separation chamber. The piston is then lifted gently as in the standard procedure, the stem cell fraction being collected at the apparition of the first platelets. The effluent line clears up again when Ficoll exits the chamber, which is the appropriate moment to stop the collection.

When the stem cells are collected by one of the methods described above adequate preservative solution can be introduced into the processing chamber by rotating the proper stopcock, the system operating in the transfer mode. It is then retransferred into the stem cell bag, its volume accurately controlled by the piston position sensor.

The bag containing the stem cell rich product can be disconnected at this stage from the rest of the set. Its volume ranges between 20–40 ml, depending of the initial volume processed. The by-products of the separation, plasma and packed red cells, can then be used for serology and HLA typing, avoiding any product loss due to sampling in the stem cell bag.

This separation system and method offer significant advantages over manual processing techniques. The disposable kit is a functionally closed system, avoiding any risk of contaminating the product during manipulation. The protocol is fully automated, through a microprocessor based control system, with ability to vary the main parameters, like centrifugation speed, centrifugation time, speed of introduction and extraction, volume to collect, etc. The volume reduction for the stem cell product represents a gain of 50% at least compared with the current state of the art. The instrumentation is very compact and portable, ideal for the decentralized processing of such procedures.

A further aspect of the invention is the use of the above-described system for processing variable volumes of biological fluid from 10 ml up to the maximum volume of the separation chamber, and for adding an additive solution to the separated components, in particular for separation of stem cells from blood and mixing the separated stem cells with a preservative solution; for separation of hematopoietic stem cells from umbilical cord blood; for separation of hematopoietic stem cells from an apheresis collection; and for separation of hematopoietic stem cells from a bone marrow aspirate.

BRIEF DESCRIPTION OF THE DRAWINGS

The invention Will be further described by way of example with reference to the accompanying drawings in which:

FIG. 9.1 to FIG. 9.6 are functional diagrams showing the various steps of umbilical cord blood separation using a disposable set including a processing chamber and a set of stopcocks according to the invention.

DETAILED DESCRIPTION OF THE SYSTEM

Figure 1:
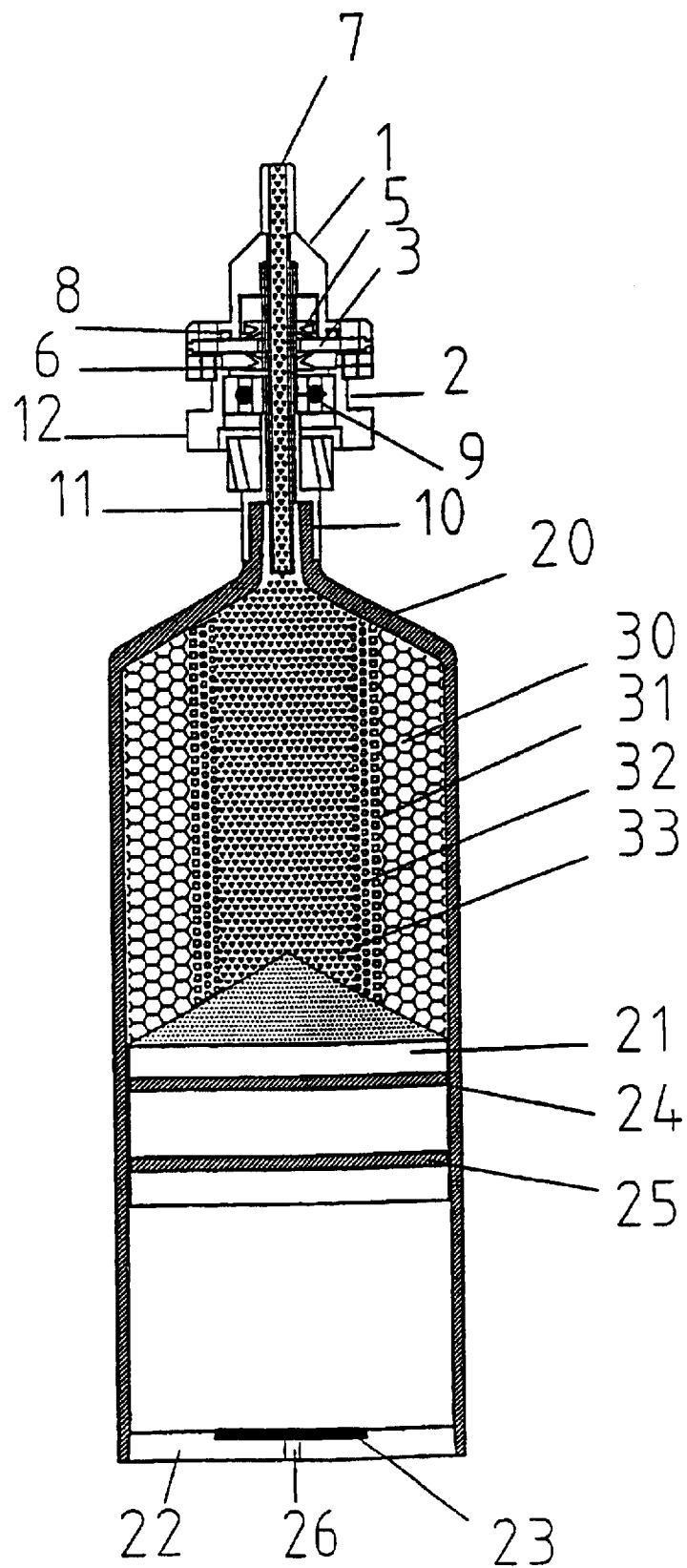
FIG. 1 is a schematic side elevation and cross-sectional view of a processing chamber and its rotary seal, showing the various sedimentation layers of blood components.

The processing chamber 20 is in accordance with that described in EP-B-0 912 250 (C. FELL). FIG. 1 is a general view of the processing chamber 20. A rotary seal 12 is located on its upper extremity 10. The rotary seal 12 is composed of an upper body 1 and lower body 2. In between is located a friction disk 3, made of a generally low friction material like polished stainless steel or ceramic. A central tubing 7 made of biocompatible material like polycarbonate is attached to the upper body 1. An O-ring 8 ensures airtightness between the upper body 2 and friction disk 3. The rotary seal 12 is mounted on a central bush 11 fitted on the upper extremity 10 of processing chamber 20. However, central bush 11 can be an integral part of chamber 20. The gap between walls of central tubing 7 and central bush 11 is small, say 0.5 mm, to provide a high rotational impedance for stopping any liquid to reach the upper extremity of bush 11. A ball bearing 9 is mounted on bush 11 to ensures the proper alignment of the processing chamber 20 when inserted into centrifuge assembly. Two rubber seals 5, 6 are located on either side of the friction disk 3, seal 5 being on the upper side and seal 6 being on the lower side. The seals 5 and 6 are of the V-seal type and ensure airtightness both in positive and negative pressure, up to at least +−0.5 bar.

Figure 2:
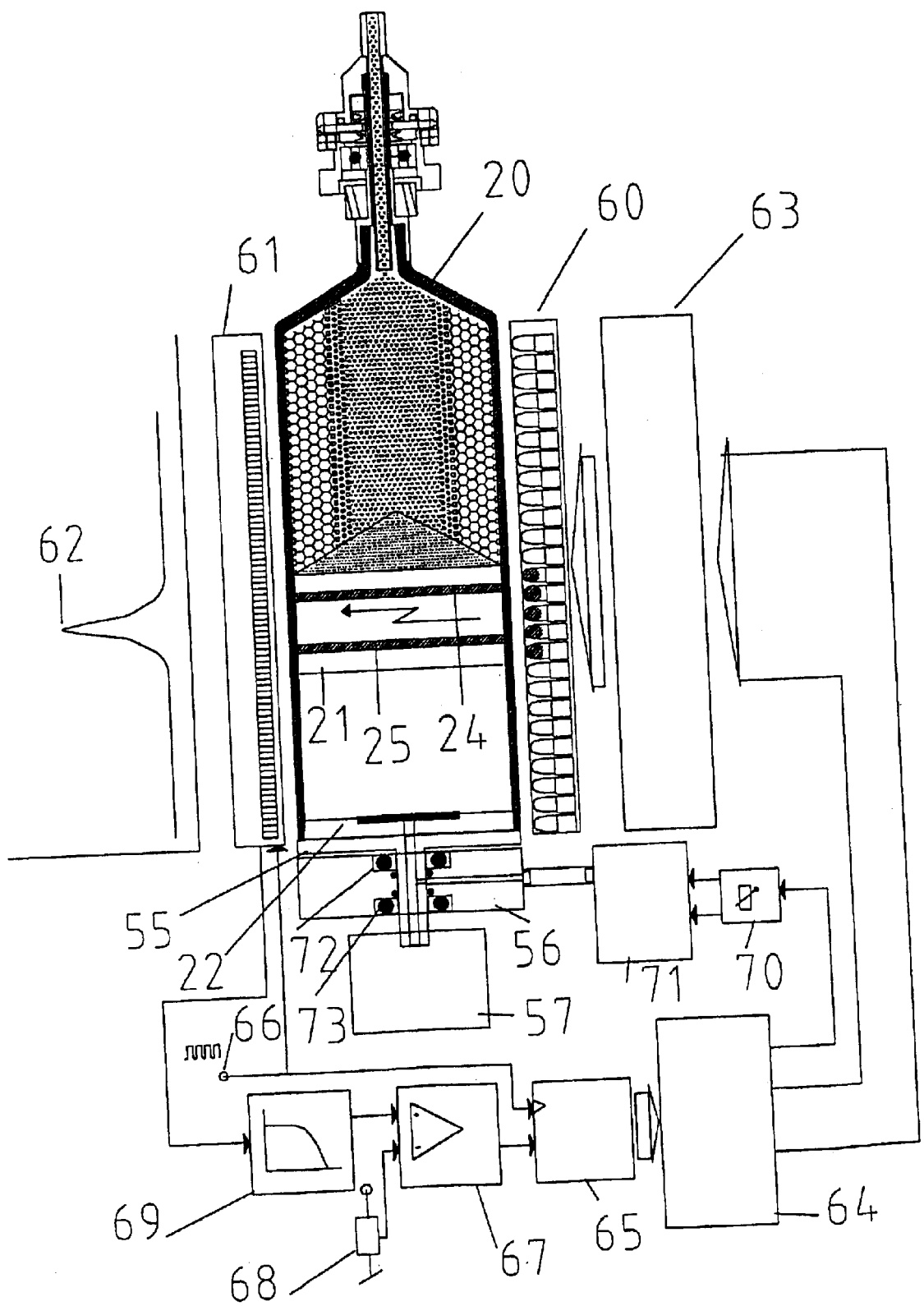
FIG. 2 is a schematic side elevation and cross-sectional view of the processing chamber and its rotary seal, associated with an optical sensor for monitoring the piston sensor, and control circuitry.

The piston 21 is made of a transparent material like polycarbonate and is equipped with two O-rings 24 and 25. These O-rings are made of low friction material like silicon. The processing chamber 20 is closed on its bottom side by a cap 22 carrying a bacterial filter 23. Air can pass through central opening 26 and filter 23 in cap 22. The position of the piston 21 can be accurately monitored by an optical sensor assembly 60 and 61 (FIG. 2). Assembly 61 is made of a vertical array of LED, preferably with light emitting in the infrared spectrum to reduce disturbance from ambient light. Only the LED facing piston 21 are turned on, in order to avoid interference from the other LED. The beam of light crosses the transparent piston 21, between the two O-rings 24 and 25. A CCD ("Charge Coupling Device") linear array 61 is placed at 180° on the other side, the exposed pixels of array 61 generating a signal 62 in the form of a peak.

Signal 62 is fed to a low-pass filter 69 and the filtered signal fed to a comparator 67 which also receives from potentiometer 68 a threshold value for discriminating the filtered signal from ambient noise. The output of comparator 67 is connected to the enable gate of counter 65. Clock signal 66 is used to intake the response from each individual pixel of the CCD linear array 61, and feed this to the input of counter 65. The output of counter 65 is connected to a CPU 64 which calculates the position of piston 21 and, when required, shifts the turned-on LEDs 60 via a multiplexer/LED driver 63. Similarly, when necessary, the CPU 64 will vary the signal of compressor driver 70 that supplies compressor 71 in order to increase or decrease pressure applied below the piston 21 to control its position.

This is only one example of position sensing for the piston 21. The light source 60 could be a filament bulb, or a unique linear source of light. The CCD linear array 61 could be replaced by an array of photosensing devices. The receiving sensing device (61) could be placed also beside the emitting light device 62, the system working in reflection light from the piston 61 rather in transmittance light through the piston 21.

The disposable Bet (FIG. 3) is composed of bags 40–44, tubing lines connected to stopcocks 45–48, and the processing chamber 20. Bag 40 contains the umbilical cord blood to process. Bag 41 contains preservative solution, generally based on a DMSO (Dimethyl Sulfoxide) solution. It is connected to the disposable set through a bacterial 0.2 micron filter 54. Bag 42 is the collection bag for the stem-cell rich product. Its plastic composition is made of a material suiting long term storage. Bag 43 is the collection bag for the plasma and bag 44 is the one for the red cells.

Figure 3:
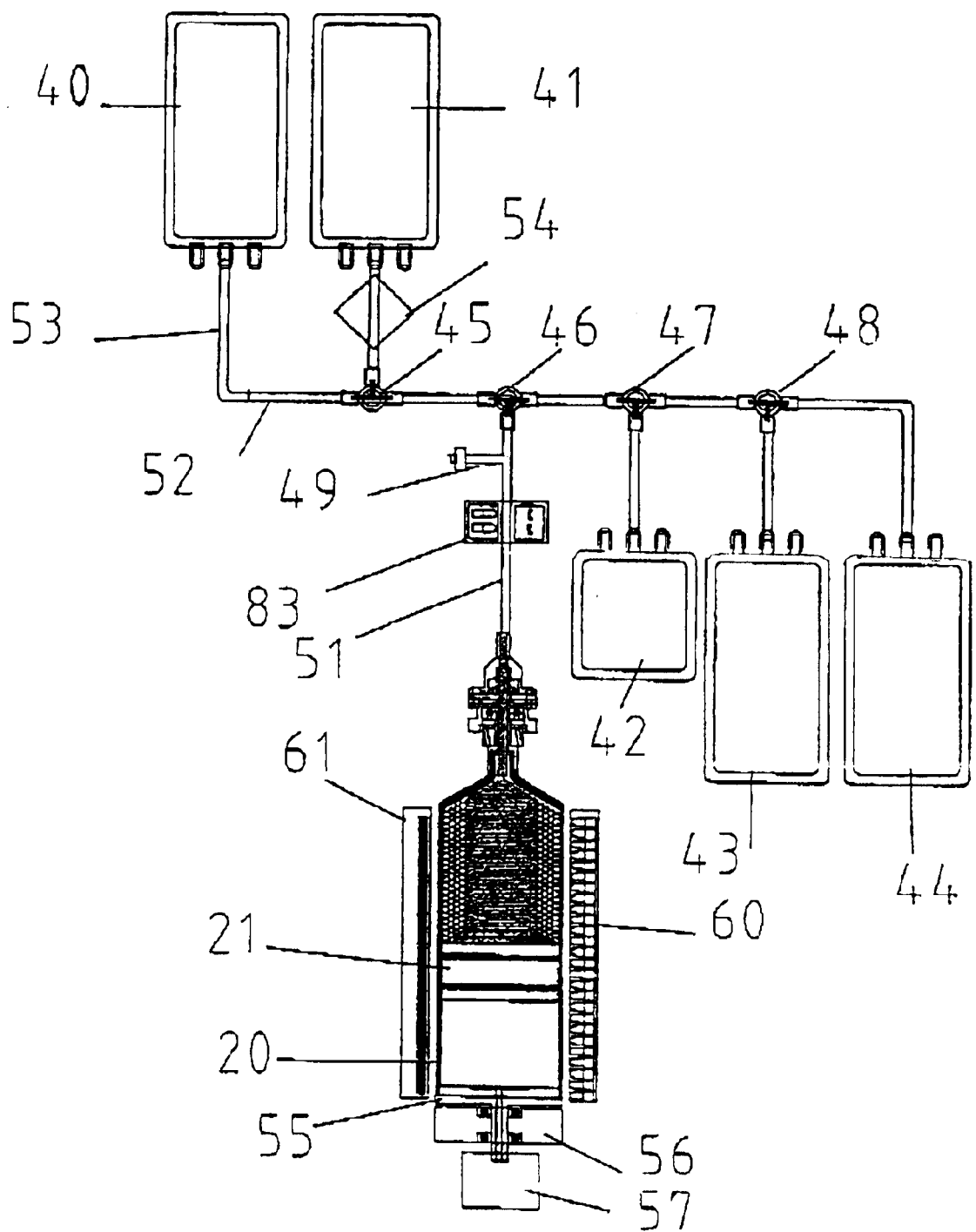
FIG. 3 illustrates in a schematic form the disposable set carrying a manifold stopcock system for the processing and separation of umbilical cord blood.
Figure 4:
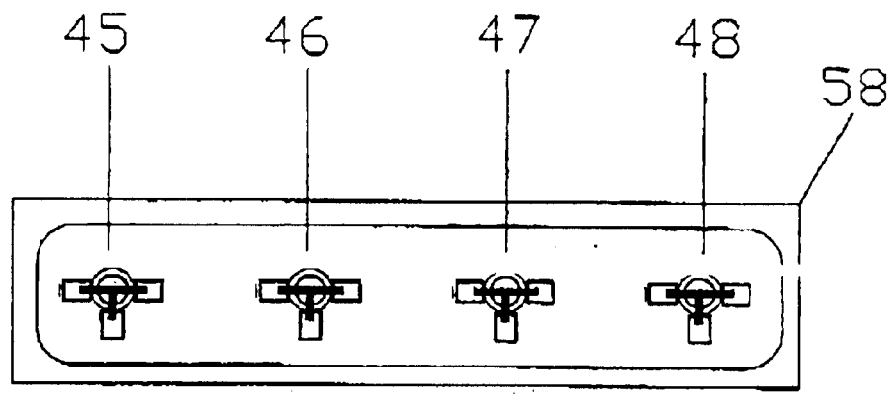
FIG. 4 illustrates in a schematic form an array of stopcocks arranged in a manifold.

FIG. 3 also shows means for rotating the chamber 20 by contacting the chamber's bottom 22 with a rotary disc 55 without any support at the chamber periphery.

Figure 5:
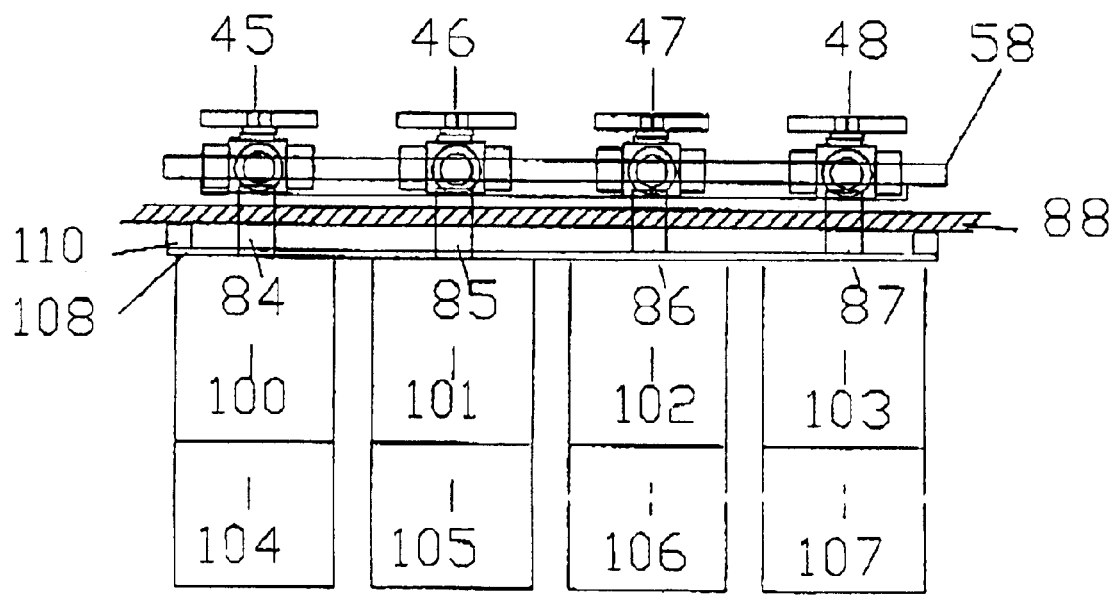
FIG. 5 is a schematic side elevation and cross-sectional view of the motor driver and control elements for rotating each individual stopcock.

An array of stopcocks 45–48 (FIG. 5) organized in a manifold 58 allows the connection between the different tubing lines. These rotational stopcocks provide an excellent cut-off between adjacent lines and ensure that no leak occurs between a closed and an open line, as is the case with tubing pinch valves. Such manifold stopcocks exist in various forms and are commercially available. The stopcocks 45–48 are driven by a set of motors 100–103. (FIG. 5). The upper shafts 84–87 of these motors engage into the bottom portion of the respective stopcocks 45–48, using passing holes through the cabinet topdeck 88. As a safety measure to allow for possible manual actuation, the shafts can engage into the stopcock in one position only, a matching indent being provided for this purpose between the shafts and the stopcock. The motors can be stepper motors or DC motors with reductors. They are equipped with position encoders 104–107, whose signals are fed back to the microprocessor control unit, ensuring that the stopcocks are correctly positioned.

Figure 6:
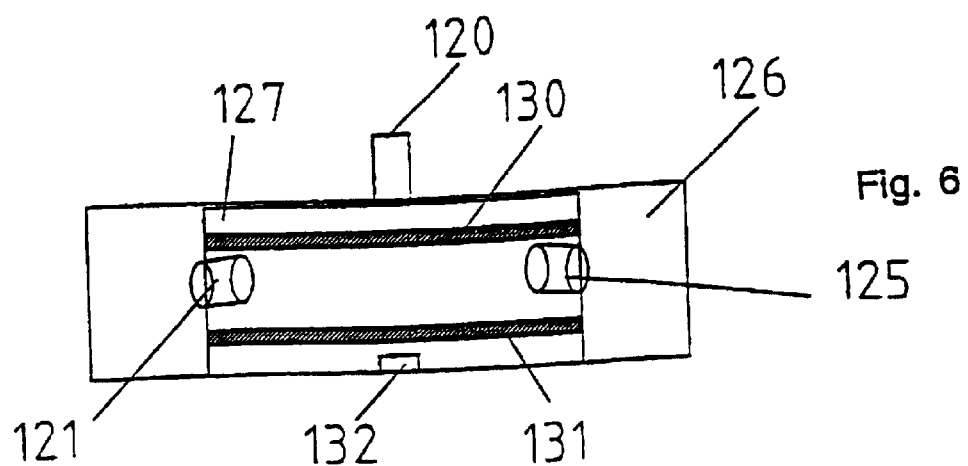
FIG. 6 is a schematic side elevation and cross-sectional view of a multiport rotational valve.
Figure 7:
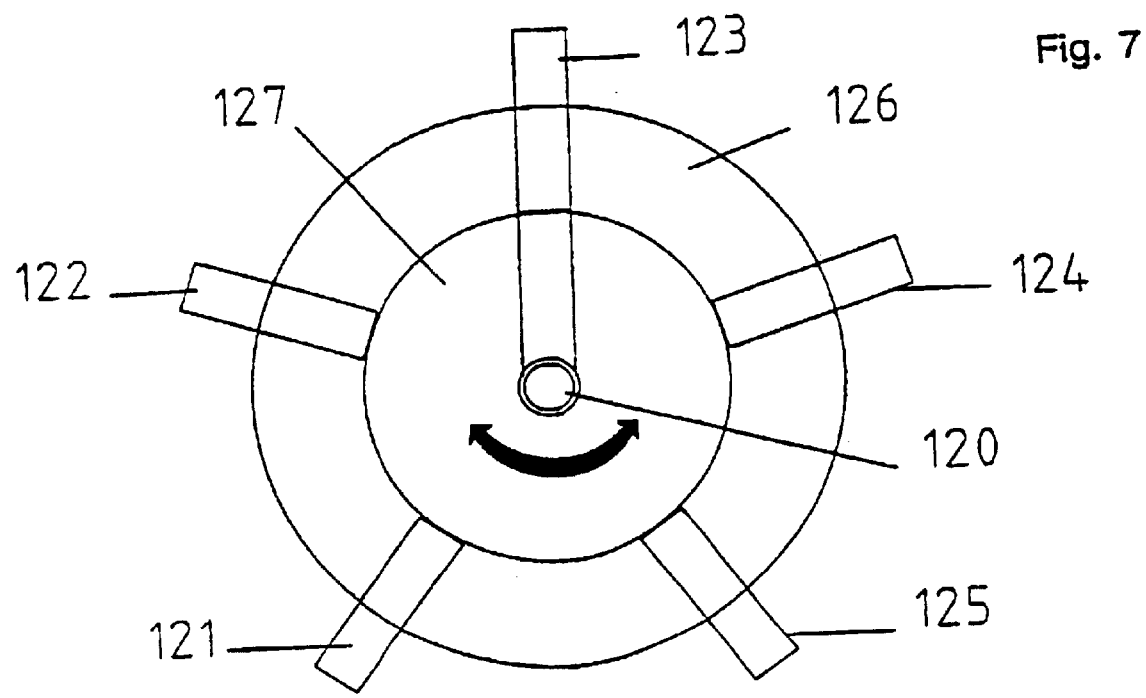
FIG. 7 schematically illustrates the multiport rotational valve of FIG. 6 with an inlet/outlet port located at the center and a range of associated ports located at the periphery.

An alternative to using a manifold stopcock is a rotational multiport valve, as shown in FIGS. 6 and 7. A central rotor 127 is inserted into a stator 126. The rotor 127 can be frictionally rotated and can be engaged on the shaft of a motor. The central port 120, connected to the processing chamber 20, can be connected to the peripheral ports 121–125 by controlled rotation with angular steps or 720. As a safety measure to allow for possible manual actuation, matching indents or other means can be provided in the rotor 127 and stator 126 for snap-holding the central port 120 in its selected angular positions aligned with the peripheral ports. A single motor is necessary to drive the rotor through the engagement recess 132. Two O-rings 130–131 ensure watertightness with the exterior (FIG. 6).

Figure 8:
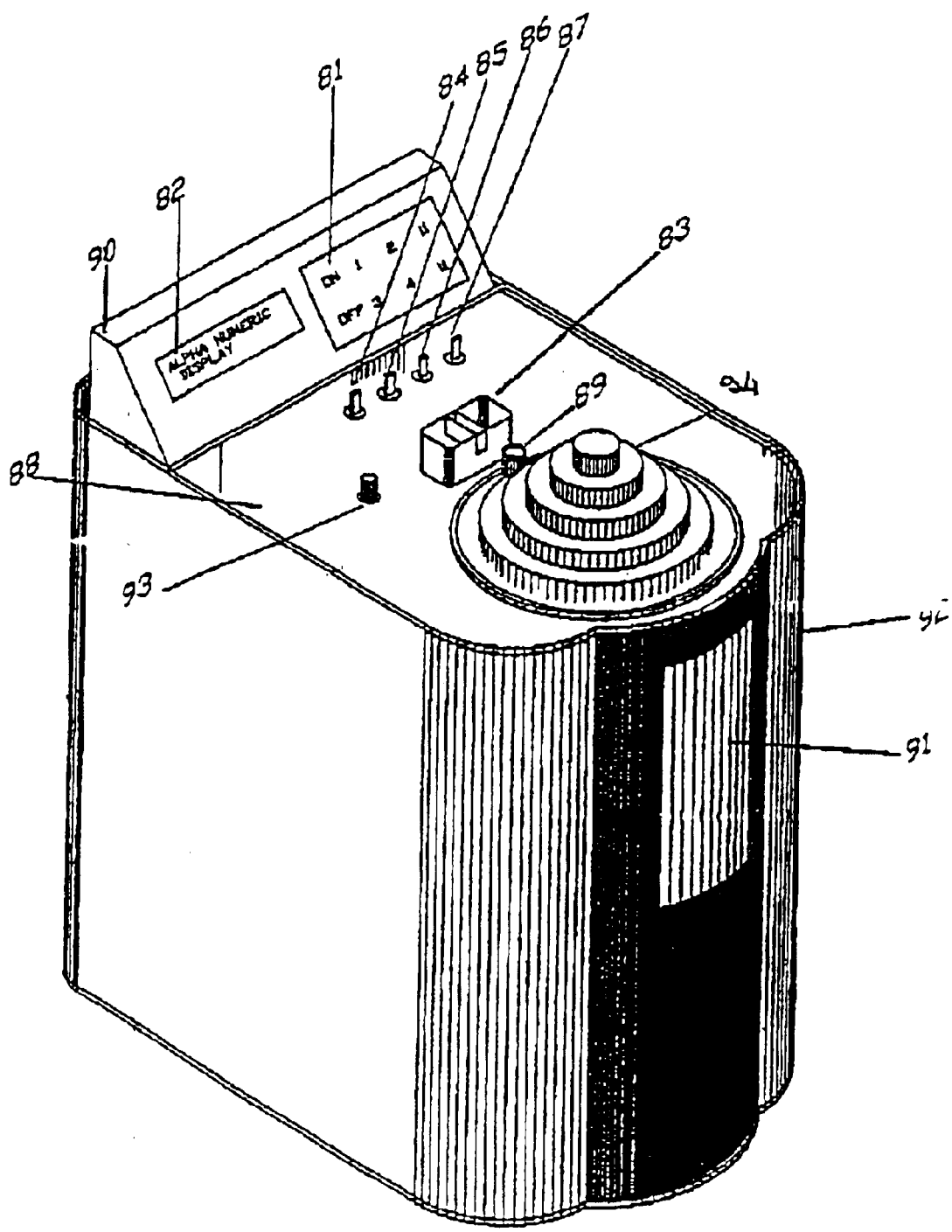
FIG. 8 is perspective view of a cabinet containing instrumentation and devices for controlling the processing.

The cabinet holding the instrumentation is shown in FIG. 8. It contains the cover 94 for holding the rotary seal 12 of processing chamber 20. The cover 94 is made of two semi-circular disks that can rotate on hinge 89. An optical line sensor 83 allows the sensing of colors in the effluent tubing 51. It holds two LED-Photosensor channels, of different wavelength like red and green, and is capable of detecting the first cells coming out of the chamber 20. It can equally detect the empty state of the effluent line tubing when liquid is introduced in the chamber. The pressure port measurement 93 receives the bacterial filter 49 located on the disposable set. This allows the monitoring of the pressure in the processing chamber 20. Upper shafts 84–87 of the stopcock driver motors 100–103 (FIG. 5) are located behind the line sensor 83. An inclined module 90 receives the display 82 for user information and a keyboard 81 for controlling the instrumentation. A window 91 is located on the front panel 92 giving visibility to the chamber piston movement.

Application for Umbilical Blood Separation

FIGS. 9.1 to 9.6 illustrate an application for umbilical cord blood separation. Bag 40 contains the umbilical cord blood rich in stem cells, recovered from the umbilical cord at birth of a child.

This bag 40 contains anticoagulant like CPD to avoid blood clots. Tubing line 53 is sterily connected to line 52 using a sterile connecting device or aseptically connected under laminar flow. However it is also possible to have the bag 40 preconnected to the whole set. The separation steps are:

Step 1 (FIG. 9.1): Stopcocks 45 and 46 are rotated to connect bag 40 to the processing chamber 20. Centrifugation starts and initially is stabilized at a speed of 4000 rpm. The pneumatic system of the instrumentation establishes a vacuum to move the piston 21 downwards. Its speed is monitored by the optical sensor assembly 61 and 62, and the vacuum level is adjusted accordingly. If the volume of the bag 40 is smaller than the processing volume of chamber 20, effluent tubing line 51 will empty, which is detected by the optical line sensor 83. The piston 21 is maintained motionless by establishing a counter pressure through the pneumatic system, and the volume intakes into chamber 20 is recorded. The centrifuge speed is gradually increased to reach 6000 rpm, with pressure increased accordingly to keep piston 21 at the same position. In the case where the volume of bag 40 is larger than the processing volume of chamber 20, piston 21 will reach the bottom of the chamber, and the pneumatic system is turned off. In both cases, after a sedimentation time of about 5–8 min, centrifuge speed is slowly decreased, while maintaining a constant counter pressure below piston 21. Stopcocks 46, 47, 48 are rotated to establish a path between the processing chamber 20 and the plasma bag 43.

Step 2 (FIG. 9.2): When the centrifuge drops to a speed generally around 4000 rpm, the piston 21 starts to move upwards, with a preset speed allowing extraction rates around 100 ml/min. This value can be modified through the program parameters. Plasma starts to be collected in bag 43. When the volume of plasma extracted reaches approximately 40% of the volume intaken, the extraction rate will be reduced by half. The first platelets contained in the buffy-coat layer start to be extracted, which is detected by light absorbance in the optical line sensor 83. At a certain level of absorbance, which can be parametered by the control program, stopcock 47 is rotated to establish the path between the processing chamber 20 and bag 42.

Step 3 (FIG. 9.3): A volume counter is triggered, and collection of a product very rich in stem cells starts. Extraction speed is always under the control of the piston optical sensor assembly 61 and 62. The volume counter value can be altered by the user in the program menu. It is chosen in order to encompass all the stem cell population, which has similar characteristics in density and size to the lymphocyte population. Such value corresponds generally to 20–30% of the intaken volume into the chamber. When this value is reached, stopcocks 47 and 48 are rotated to establish a path with bag 44.

Step 4 (FIG. 9.4): Centrifugation is generally stopped at this stage, and pressure diminished to allow a smooth extraction of the remaining red cells into bag 44. This phase is completed when piston 21 reaches the top of the processing chamber 20, detected by the piston optical sensor assembly 61 and 62. At this stage, if the bag 40 is not empty, the process will be resumed at Step 1, otherwise it will proceed with Step 5, which is the transfer mode. An optional phase is to further separate the stem cell product by returning the content of bag 42 into the processing chamber 20, centrifuging the product once again and expressing its separated components to bags 43, 42 and 44 as before.

Step 5 (FIG. 9.5): Stopcocks 45 and 46 are rotated in order to establish a path between the preservative solution bag 41 and the processing chamber 20. The preservative solution is generally a composition based on 10 or 20 vol % DMSO chemical solution, which can contain also a phosphate buffer. The centrifuge being idle, piston 21 is moved downwards by establishing a vacuum with the pneumatic system. The volume intaken is a proportion of the volume counter described in Step 4. When this proportion is reached the vacuum stops and stopcocks 46 and 47 are rotated in order to establish a path between the processing chamber 20 and the stem cell bag 42.

Step 6 (FIG. 9.6): The pneumatic system is turned down, and piston 21 moved upwards. The preservative solution is added to the content of the stem cell bag 42. This transfer phase is completed when the piston reaches the top of the processing chamber 20, detected by the piston optical sensor assembly 61 and 62. An optional additional phase can be added if the stem cell product needs to be diluted further with plasma. In this case Steps 5 and 6 will be repeated, with the difference that the transfer will be established between the plasma bag 43, the processing chamber 20 and the stem cell bag 42.

When all the steps described above are completed, all the stopcocks can be rotated at a 45° angle in order to close all the communicating ports. The bags 42–44 can be disconnected from the rest of the set, which can be discarded at this stage. The stem cell bag 42 is then ready for conveying to a separate storage unit, the by-products plasma in bag 43 and red cells 44 being used for HLA typing and quality control assessments.

It will be appreciated that including a transfer mode, i.e. steps 5 and 6, opens up new applications for the system that were not available when the apparatus operated solely in the separation mode, in particular for applications requiring adding an additive solution to the separated components.

It is to be understood that this invention may be embodied in several different forms without departing from its spirit of essential characteristics. The scope of the invention is defined in the appended claims, rather than in the specific description preceding them. All embodiments that fall within the meaning and range of equivalency of the claims are therefore intended to be embraced by the claims.

Moreover, the novel optical control device (60–71) herein described, as well as the arrangement of stopcocks (45–48) and tubing, the multiport valve (FIGS. 6 and 7), the special rotatable seal (1–7) for positive and negative pressure operation, and the special axial bearings mounting the chamber 20, permitting drive without a holding chuck, can all advantageously be used in different systems.

What is claimed is:

1. A system for the processing and separation of biological fluids into components, comprising a set of containers for receiving the biological fluid to be separated and the separated components, and optionally one or more additional containers for additive solutions, and a hollow centrifugal processing chamber rotatable about an axis of rotation and having an axial inlet/outlet for the biological fluid to be processed and for the processed components of the fluid, the processing chamber containing an axially movable member which defines a separation space of variable size for receiving biological fluid, the member being axially movable to intake a selected quantity of biological fluid to be processed into the separation space via said inlet and to express processed biological fluid components from the separation space via said outlet, and means for monitoring the position of the axially movable member to thereby control the amount of intaken biological fluid and the expression of separated components, the system further comprising a distribution valve arrangement for establishing selective communication between the processing chamber and selected containers or for placing the processing chamber and containers out of communication, the system comprising means for controlling operation of the system in two operational modes, a separation mode and a non-separation transfer mode, wherein:

in the separation mode fluids can be intaken into the processing chamber while the chamber is rotating or stationary, fluid intaken into the chamber is centrifuged and separated into components, and the separated components expressed while the chamber is rotating or, optionally, for the last separated component, while the chamber is stationary; and in the transfer mode the processing chamber intakes fluid and expresses fluid with the chamber stationary, the valve actuation arrangement being actuable to transfer amounts of fluid from one container to another via the processing chamber, by axially moving the member, without centrifugation or separation of the fluid into components, and said means for monitoring the position of the axially movable member controls the amounts of non-separated fluids transferred.

2. The system of claim 1, wherein the distribution valve arrangement comprises a set of rotational stopcock valves arranged in a manifold array, or a multiport rotational valve.

3. The system of claim 1, wherein the distribution valve arrangement comprises a plurality of stopcock valves connected to tubing lines interconnecting the set of containers, the optional additional containers, the processing chamber and further stopcock valves, each stopcock valve comprising a rotatable stopcock valve member having a shaft associated with drive means, said shaft being rotatable to selectively connect or disconnect the stopcock valve's tubing lines.

4. The system of claim 3, comprising means for allowing insertion of each stopcock valve only in a defined angular alignment of the rotatable stopcock valve member.

5. The system of claim 1, wherein the distribution valve arrangement comprises a multiport valve comprising a central rotor rotatably mounted in an annular stator, the rotor having a central port connected to the processing chamber and leading to the rotor outer periphery, and the stator having a plurality of ports at selected angular locations each connected to a container and each leading into the inner periphery of the annular stator, the central port of the rotor being connectable to selected ports of the stator, or disconnected, by rotation of the rotor.

6. The system of claim 1, wherein the movable member is a piston fluid-tightly movably mounted in a generally-cylindrical centrifugal processing chamber.

7. The system of claim 6, further comprising optical means for monitoring the position of the piston, comprising an alignment of light emitting elements generally parallel to the piston axis, and an alignment of light receiving elements generally parallel to the piston axis, the receiving elements being arranged to receive light from the emitting elements transmitted through or past the piston or reflected by the piston, and to deliver a signal representative of the piston's position.

8. The system of claim 7, wherein the receiving elements are arranged to deliver said signal to means for moving the piston and means for controlling the piston's position.

9. The system of claim 1, comprising an optical sensor monitoring fluid in the tubing line connected to the axial inlet/outlet, for stopping the intake of biological fluid when the tubing line is empty during the intake mode and/or for providing a signal for switching the distribution valve arrangement in the extraction mode.

10. The system of claim 1, wherein the axial inlet/outlet comprises a rotatable seal mountable in a stationary housing, said seal being operable for positive and negative pressure conditions in the rotatable chamber.

11. The system of claim 1, wherein the processing chamber is mounted for rotation about its axis by means of bearings at opposite ends of the chamber, one end of the chamber being associated with means for rotating the chamber by contacting the chamber's bottom with a rotary disc without any support at the chamber periphery.

12. The system of claim 1, wherein the means for controlling operation of the system in said two operational modes comprises a microprocessor based control system controlling an automated protocol.

13. A method of processing and separating biological fluids in a system according to claim 1, the method comprising:

separating a biological fluid with the system operating in the separation mode, by intaking fluid into the processing chamber while the chamber is rotating or stationary, centrifuging fluid intaken into the chamber to separate the fluid into components, and expressing the separated components while the chamber is rotating or possibly, for the last component, while the chamber is stationary; and transferring fluid between containers with the system operating in the transfer mode, by intaking fluid into the processing chamber with the chamber stationary, actuating the valve distribution arrangement to transfer an amount of fluid from one container to another via the processing chamber, by moving the member, without centrifugation or separation of the fluid into components, and monitoring the position of the movable member to control the amount of non-separated fluid transferred.

14. The method of claim 13, wherein a component of the biological fluid is separated into a given container, the amount of said component separated into the given container being controlled by monitoring the position of said member, and an additive solution is transferred from an additional container to said given container via the processing chamber in said transfer mode, the amount of additive solution transferred being calculated as a function of the amount of said separated component in the given container.

15. The method of claim 13, wherein a density gradient product and blood are introduced into the processing chamber, and a component of the biological fluid is separated into a given container and its collection is completed when the density gradient appears.

16. The method of claim 13, wherein operation of the system in said two operational modes is controlled according to an automated protocol by a microprocessor based control system.

17. A disposable set for collecting and separating selected quantities of biological fluids comprising the centrifugal processing chamber of a system according to claim 1, wherein the inlet/outlet of the centrifugal processing chamber is connected to a container of biological fluid, an additional container containing an additive solution, a plurality of containers for receiving the separated components of the biological fluid, interconnected by a distribution valve arrangement comprising a set of rotational stopcock valves arranged in a manifold array, or a multiport rotational valve.

18. The disposable set of claim 17, wherein the distribution valve arrangement comprises a plurality of stopcock valves connected to tubing lines interconnecting the set of containers, the optional additional containers, the processing chamber and further stopcock valves, each stopcock valve comprising a rotatable stopcock valve member having a shaft associated with drive means, said shaft being rotable to selectively connect or disconnect the stopcock valve's tubing lines.

19. The disposable set of claim 17, wherein the distribution valve arrangement comprises a multiport valve comprising a central rotor rotatably mounted in an annular stator, the rotor having a central port connected to the processing chamber and leading to the rotor outer periphery, and the stator having a plurality of ports at selected angular locations each connected to a container and each leading into the inner periphery of the annular stator, the central port of the rotor being connectable to selected ports of the stator, or disconnected, by rotation of the rotor.

20. The method of claim 14, wherein variable volumes of biological fluid from 10 ml up to the maximum volume of the separation chamber are processed and an additive solution is added to the separated components.

21. The method of claim 13, wherein the fluid is blood and the separated component is stem cells and a preservative solution is mixed with the stem cells.

22. The method according to claim 21, wherein the stem cells are hematopoietic stem cells from umbilical cord blood, from an apheresis collection, or from a bone marrow aspirate.

* * * * *